(12) United States Patent
Mednikov et al.

(10) Patent No.: US 6,479,990 B2
(45) Date of Patent: Nov. 12, 2002

(54) EDDY CURRENT SENSOR FOR ANALYZING A TEST OBJECT AND METHOD OF OPERATING SAME

(75) Inventors: Felix Mednikov, Ortenburg (DE); Roland Mandl, Ortenburg (DE); Mark Netschaevsky, Samara (RU)

(73) Assignee: Micro-Epsilon Messtechnik GmbH & Co. KG, Ortenburg (DE)

(*) Notice: Subject to any disclaimer, the term of this patent is extended or adjusted under 35 U.S.C. 154(b) by 0 days.

(21) Appl. No.: 09/883,773

(22) Filed: Jun. 18, 2001

(65) Prior Publication Data

US 2001/0054896 A1 Dec. 27, 2001

Related U.S. Application Data

(63) Continuation of application No. PCT/DE99/03558, filed on Nov. 6, 1999.

(30) Foreign Application Priority Data

Dec. 18, 1998 (DE) .......................... 198 58 754
Feb. 26, 1999 (DE) .......................... 199 08 360

(51) Int. Cl.$^7$ .......................... G01N 27/72; G01R 33/00
(52) U.S. Cl. .................. 324/225; 324/229; 324/207.12
(58) Field of Search ................. 324/225, 229, 324/233, 239, 232, 230, 207.16, 207.12

(56) References Cited

U.S. PATENT DOCUMENTS

| | | | |
|---|---|---|---|
| 4,303,885 A | | 12/1981 | Davis et al. |
| 4,771,238 A | * | 9/1988 | Caruso et al. ............... 324/229 |
| 4,810,966 A | * | 3/1989 | Schmall ................ 324/207.17 |
| 5,343,146 A | * | 8/1994 | Koch et al. ................. 324/230 |
| 5,541,510 A | | 7/1996 | Danielson |
| 5,889,401 A | | 3/1999 | Jourdain et al. |
| 6,040,694 A | | 3/2000 | Becker |
| 6,288,536 B1 | | 9/2001 | Mandl et al. |

FOREIGN PATENT DOCUMENTS

| | | |
|---|---|---|
| DE | 196 10 844 A1 | 10/1996 |
| DE | 196 28 220 A1 | 2/1998 |
| DE | 196 31 438 A1 | 2/1998 |
| JP | 61 096401 A | 5/1986 |
| JP | 63 311103 A | 12/1988 |
| WO | WO 97/23762 A2 | 7/1997 |

\* cited by examiner

*Primary Examiner*—Edward Lefkowitz
*Assistant Examiner*—Subhash Zaveri
(74) *Attorney, Agent, or Firm*—Alston & Bird LLP

(57) ABSTRACT

A method for operating an eddy current sensor (10) with a measuring coil (2) and an evaluation circuit (4) for determining material or geometric parameters of a test object (5), in which the test object (5) is arranged at a distance (d) from the measuring coil (2). The impedance of the measuring coil (2) is evaluated, while the measuring coil (2) is being supplied with an alternating voltage of a predetermined frequency, and the evaluation circuit (4) determines the material and geometric parameters of the test object (5) based on the impedance of the measuring coil (2). The impedance of the measuring coil (2) is determined at an alternating voltage of a first frequency, and the impedance of the measuring coil (2) is determined at an alternating voltage of a second frequency, and the evaluation circuit (4) computes the material and geometric parameters of the test object (5) on the basis of the impedances of the measuring coil (2) at the first and the second frequencies. An eddy current sensor (1) is also disclosed, which can be used with advantage in conjunction with the method.

32 Claims, 4 Drawing Sheets

EDDY CURRENT SENSOR FOR ANALYZING A TEST OBJECT AND METHOD OF OPERATING SAME

CROSS REFERENCE TO RELATED APPLICATION

This is a continuation of international application No. PCT/DE99/03558, filed Nov. 6, 1999, and designating the U.S.

BACKGROUND OF THE INVENTION

The invention relates to a method for operating an eddy current sensor with a measuring coil and an evaluation circuit for determining material or geometric parameters of a test object, wherein the measuring object is arranged at a distance from the measuring coil, wherein the impedance of the measuring coil is evaluated, while the measuring coil is being supplied via an alternating voltage of a predetermined frequency, and wherein the evaluation circuit determines the material and geometric parameters of the test object on the basis of the impedance of the measuring coil.

The invention further relates to an eddy current sensor, in particular for use in the present method, with a measuring coil, a compensation coil, and an evaluation circuit, used for determining the material and/or geometric parameters of an electrically conductive test object. The measuring coil and compensation coil can be supplied with alternating current, and the compensation coil is arranged in the vicinity of the measuring coil, so that it is exposed to the thermal environmental conditions of the measuring coil.

Eddy current sensors are frequently used in the industry for measuring the distance and for measuring the thickness on a flat test object, for example, a web, a layer, or a tape. In this process, they are used in most cases under difficult environmental conditions, for example, at high temperatures. Just in connection with high, strongly fluctuating temperatures, considerable falsifications of the measuring and evaluation results occur in known processes for determining material and geometric parameters. While in a measuring coil of the eddy current sensor, the temperature influence leads primarily to a change of the real part, it is also possible to detect an influence on the imaginary part of the complex impedance. However, on the other hand, the temperature has also an influence on the conductivity of the test object. Since the conductivity of the test object in turn exerts an influence on the induced eddy currents and, likewise, via the feedback of the magnetic coupling, on the impedance of the measuring coil, the conductivity of the test object is likewise a source for falsifying the measuring results.

U.S Pat. No. 6,288,536 discloses an eddy current sensor with a measuring and a compensation coil, which is arranged in the direct vicinity of, i.e., in thermal contact with the measuring coil. The electromagnetic fields of the compensation coil and the measuring coil are oriented in orthogonal relationship with each other. As a result of the orthogonal arrangement of the compensation coil, the test object has little influence on the impedance thereof, in case the eddy current sensor is positioned with its measuring coil such that the presence of the test object becomes maximally active on the impedance of the measuring coil.

A disadvantage of the known eddy current sensor lies in that the temperature influences on the conductivity of the test object are transferred, via the eddy current effect, into the measuring coil, so that the measuring results, for example, of the thickness of a layer, are influenced by the change of conductivity.

Furthermore, eddy current sensors are known, which are used in a method for a noncontacting measurement of the thickness of a foil, wherein the eddy current sensor is arranged on one side of the test object. This method has the disadvantage that as a function of the material properties, the eddy current sensor must be kept at a certain readjustable basic distance from the test object to perform exact measurements.

It is therefore an object of the invention to describe a method and an miniaturizable eddy current sensor for a noncontacting measurement of material and geometric parameters of electrically conducting materials, which provides a reliable compensation for disturbance variables on the measuring results. A disturbance variable means the impedance fluctuation of the measuring coil by changing the basic distance or the temperature, whereby the measuring results are influenced in a falsifying manner.

SUMMARY OF THE INVENTION

The above and other objects and advantages of the invention are achieved by the provision of a method of operating an eddy current sensor wherein the impedance of the measuring coil is measured at an alternating voltage of a first frequency, the impedance of the measuring coil is measured at an alternating voltage of a second frequency, and the evaluation circuit computes the material and geometric parameters of the test object based on the impedances of the measuring coil at the first and the second frequencies.

In accordance with the invention, it has been recognized that the temperature influences on the measurement of the material and geometric parameters of the test object can be excellently compensated, when the measurement is performed with an eddy current sensor at two different frequencies. The temperature influences are differently effective as a function of the frequency of the alternating voltage, which is supplied to the measuring coil. On the other hand, based on the impedances of the measuring coil at the different frequencies, with the knowledge of the mathematical relationships between temperature-influenced variables, for example, the conductivity of the test object, the evaluation circuit is capable of computing the material and geometric parameters of the test object. A complete compensation of the temperature influences affecting the measured values is possible, only when both the temperature influence on the impedance of the measuring coil and the temperature influence on the conductivity of the test object are compensated.

It is preferred to use the method of the present invention in connection with unilaterally measuring the thickness of a foil, with the eddy current sensor being arranged on one side of the test object. The method includes determining the thickness or strength of a flat test object, in particular a web, a tape, or a layer of an electrically conducting material, with the aid of at least one measuring coil through which an alternating current passes, the measuring coil being arranged at a basic distance from the test object. In so doing, the change of inductance and damping are evaluated via the impedance. As regards the basic distance, it is possible to perform first a measurement with the eddy current sensor without test object for purposes of calibrating the eddy current sensor. Thereafter, it is possible to perform measurements with the test object, wherein it is intended, in accordance with the invention, to compensate the impedance fluctuations resulting from the variation of the basic distance. The method of the present invention permits a calibration, even when measurements can be performed only with the test object. In this instance, a microcontroller may compute the compensated measured value from the measurement results at the different frequencies.

In accordance with the invention, the method may provide for the following measuring steps: determining the impedance, or the inductance value, and/or the damping value of the measuring coil at a first frequency. In this instance, either the test object is absent in the region of the eddy current sensor, or the spacing between the test object and measuring coil is greater than twice the radius R of the measuring coil, so that the influence of the measuring object is small. Subsequently, the inductance value and the damping value are determined in the presence of the test object, with the spacing between the measuring coil and the test object being smaller than the radius R of the measuring coil. Preferably, the measuring results are converted into a dimensionless value. Finally, a computer determines the thickness of the test object from the measured value of the measuring coil. To this end, one may use in the computation, for example, the conductivity of the test object. However, when conducting the measurement exactly in accordance with the invention at two different frequencies, it will not be absolutely necessary to determine the conductivity, inasmuch as the computer MC subsequent to the eddy current sensor is capable of computing the thickness of the test object by an algorithm, which is independent of the conductivity and/or basic distance between the measuring coil and the test object.

A further development of the invention permits computing the thickness D of a flat test object from the measured value. In the case of a known, for example, previously measured conductivity of the test object, it is possible to determine the thickness from the following equations:

$$D \approx konst. * \tan\varphi_c = -\frac{\varphi_2(\xi, \beta)}{\varphi_1(\xi, \beta)} \quad \xi = \frac{2d}{r} \quad \beta = r\sqrt{\mu_o \omega \sigma}$$

$$\psi_1(\xi,\beta) = \tfrac{1}{2}[\tfrac{1}{2}(ch(\xi m) - \cos(\xi n)) + m*sh(\xi m) + n*\sin(\xi n)]$$

$$\psi_2(\xi,\beta) = mn(ch(\xi m) - \cos(\xi n)) + \tfrac{1}{2}(n*sh(\xi m) - m*sh(\xi m) - m*\sin(\xi n))$$

$$m = \frac{1}{\sqrt{2}}\sqrt{\sqrt{\frac{81}{16} + \beta^4} + \frac{9}{4}} \quad n = \frac{1}{\sqrt{2}}\sqrt{\sqrt{\frac{81}{16} + \beta^4} - \frac{9}{4}}$$

In the foregoing equations, D is the thickness of the test object, d the distance from the coil to the test object, r the radius of the coil, ω the angular frequency, and $\mu_o$ the magnetic field constant of the measuring coil.

In accordance with the invention, the evaluation circuit is able to compute the thickness of the measuring object by means of the foregoing equations from the impedances of the measuring coil. In this instance, the conductivity σ of the test object must be known. This method may be used in accordance with the invention in the case of an eddy current sensor with or without a compensation coil.

Preferably, the conductivity of the test object may be computed by the evaluation circuit based on the impedance of the measuring coil measured at a first frequency. The advantage in the case of this method lies in that the conductivity of the test object need not be determined before each measuring operation to compute the thickness D of the test object. Based on the foregoing equations, the evaluation circuit is able to compute the conductivity of the test object.

In a preferred further development of the invention, the measuring coil is supplied with an alternating voltage of a high, first frequency, so that at this first frequency the impedance of the measuring coil is nearly independent of the material or geometric parameters of the object. When the first frequency is selected large enough, the impedance of the measuring coil will be independent of the material or geometric parameters, in particular the thickness of the flat test object. This is very advantageous for determining the material or geometric parameters of the test object without computing the temperature-dependent conductivity of the test object. Since in this instance the determination of the thickness of the test object is independent of the conductivity of the test object, the temperature influences on the test object will thereby be compensated.

In a particularly advantageous manner, it is also possible to use, together with the method, an eddy current sensor with a compensation coil. In this instance, the compensation coil itself is capable of reducing the temperature influences on the measuring coil. Thus, the compensation coil is arranged such that it is independent of the material or geometric parameters of the test object. The impedance of the compensation coil can then be compared with the impedance of the measuring coil, balanced, or offset, so that the temperature-dependent influence on the measuring coil is additionally compensated by the especially advantageous eddy current sensor of this invention. When using the method together with the eddy current sensor of the present invention, both the temperature influences on the conductivity of the test object and the temperature influences on the measuring coil itself will be compensated.

In a particularly advantageous further development of the invention, the material and geometric parameters of the measuring object are computed by the evaluation circuit, in particular by a computer, by means of a nonlinear equation system. For computing the thickness of a test object, the equation system is as follows:

$$\tan\varphi_c(\omega_k) = -\frac{\varphi_2(\xi, \beta_k)}{\varphi_1(\xi, \beta_k)}$$

If the equation is equated on the one hand for the first frequency (k=1) with the equation for the second frequency (k=2), it will be possible to compute therefrom the conductivity of the test object in a particularly advantageous manner. In this instance, the variable $\omega_K$ is the angular frequency of the alternating voltage, which is supplied to the measuring coil. Preferably, the nonlinear equation system is dependent on the first frequency and the second frequency of the alternating voltage. Since it is possible to compute the conductivity from the equation system, it can be used for computing the material or geometric parameters of the test object, in particular the thickness of a flat test object.

In a particularly advantageous further development of the method according to the invention, it is possible to determine by approximation the thickness of a test object in a limited range. In this measuring range, the thickness D of a flat test object can be computed via the following equation:

$$D \approx konst. * \tan\varphi_c =$$

$$-2\beta_k \frac{2\sqrt{2}\,\beta_k(ch(\delta_k) - \cos(\delta_k)) + 3(sh(\delta_k) - \sin(\delta_k))}{3\sqrt{2}\,(3ch(\delta_k) - 2\cos(\delta_k)) + 2\beta_k(sh(\delta_k) + \sin(\delta_k))},$$

$$\delta_k = \frac{\xi, \beta_k}{\sqrt{2}}$$

It is preferred to limit the approximate computation of the material or geometric parameters of the test object by the evaluation circuit to a range as a function of the conductivity of the test object and the frequencies. The range, to which the computation of the evaluation circuit is limited, can be represented by the following equation:

$$r = \sqrt{\omega_k \mu_O \sigma_k} \geq 10$$

In a particularly advantageous further development of the invention, the temperature influences on the impedance of the measuring coil are balanced by a compensation coil, whose impedance is nearly independent of the material and geometric parameters of the test object. The impedance of the compensation coil may be used for compensating the temperature influences in the case of the impedance of the measuring coil. To this end, the evaluation circuit may include, for example, means for computing the corrected real part of the measuring coil. The corrected real part results from the difference between the real parts of the impedances of the measuring coil and the compensation coil.

In addition, the evaluation circuit may include means for determining the corrected imaginary part as a difference between the imaginary part of the impedances of the measuring coil and the compensation coil. In this manner, the evaluation circuit is able to compensate the temperature influence on the measuring coil by subtracting the impedance of the compensation coil. On the other hand, however, it would also be possible to compensate the temperature influence in that the temperature influence at the first frequency has a different effect than at the second frequency. Consequently, it would also be possible to compensate the temperature influence via the impedances at the first and the second frequency of the supplied alternating voltage.

In another further development of the present invention, the quality of the measuring coil and that of the compensation coil are adapted in their respective amount. The equation for the quality of the coils is:

$$Q = \frac{\omega L}{R}$$

In a preferred further development of the invention, the quality of the measuring coil is equal to the quality of the compensation coil.

The adaptation of quality of the coils can be achieved by a corresponding selection of the coil parameters. The coil quality may be adjusted, for example, via the number of winds, via the diameter of the coil wire, or via the coil geometric.

In a particularly preferred further development of the invention, the computation of the material and geometric parameters of the test object, in particular the thickness, is independent of the spacing between the measuring coil and the test object. This allows the evaluation circuit to compute the thickness of the test object without having to know the spacing between the test object and the measuring coil.

It is preferred to compensate the temperature by subtracting the complex impedance of the measuring coil from the complex impedance of the compensation coil. To this end, it is possible to provide two operational amplifiers with the measuring coil and the compensation coil interposed in the respective feedback loop.

In another further development of the invention, it is possible to use the amplitude of the coupling impedance of the measuring coil or the compensation coil for a numerical correction or improvement of the computation.

The object of the present invention is also achieved by the provision of an eddy current sensor which has a measuring coil, a compensation coil, and an evaluation circuit for determining material and/or geometric parameters of an electrically conducting test object. The measuring coil and compensation coil can be supplied with an alternating current, and the compensation coil is arranged in the vicinity of the measuring coil, so that it is exposed to the thermal environmental conditions of the measuring coil. In accordance with the invention, the compensation coil is designed and arranged in such a manner that the influence of the test object on its impedance is as little as possible.

In accordance with the invention, it has been recognized that in an eddy current sensor with a compensation coil, the influence of the test object on the impedance thereof should be as little as possible, so that the evaluation circuit is able to subtract the temperature-dependent impedance of the compensation coil from the temperature-dependent and test-object-dependent impedance of the measuring coil, and that the thus remaining difference amount essentially depends only on the influence by the test object. For example, the compensation coil may be arranged such that its coil section is oriented at an angle with the coil section of the measuring coil, so that a differing feedback of the test object to the compensation coil results, when compared with the measuring coil.

However, even when the axes of the measuring coil and compensation coil are arranged substantially parallel, the evaluation circuit will be able to compensate the temperature influence. For example, in this instance, the compensation coil has a much smaller cross section than the measuring coil, whereby the influence of the test object on the compensation coil is greatly reduced. In this case, the temperature influence has a similar effect on both coils. Consequently, it is possible to subtract the impedance of the compensation coil from the impedance of the measuring coil for purposes of compensating for temperature, so that the difference value depends only on the influence of the test object. Naturally, it is also possible to generate, via the number of coil winds, the coil geometric, or the coil quality, an impedance that is differently dependent on the test object.

In a particularly advantageous further development of the invention, the compensation coil is arranged inside the measuring coil. For this reason, the eddy current sensor is especially suited for a compact construction. In this instance, the radius of the compensation coil is selected in particular smaller than the radius of the measuring coil. As a result of the different dimensioning of the coils, it is possible to keep the influence of the test object on the compensation coil smaller than the influence on the measuring coil. In this manner, the subtraction of the impedance of the compensation coil from the impedance of the measuring coil makes it possible to perform an advantageous temperature compensation.

Preferably, the radius of the compensation coil is smaller than the radius of the measuring coil, and in particular smaller than the spacing between the compensation coil and the test object. In this geometric configuration and arrangement of the compensation coil, the influence of the test object on the impedance of the compensation coil is relatively small. Consequently, the evaluation circuit is able to perform the computation of the temperature compensation in a particularly advantageous manner.

The compensation coil and/or the measuring coil of the eddy current sensor according to the invention may also be designed and constructed as flat coils. In connection with the invention, a flat coil is understood to be a spiral coil or a coil, whose winds extend substantially in one plane, but which may also be multilayered perpendicularly to the plane. This allows to arrange both the measuring coil and the compensation coil on one or more printed circuit boards or similar carrier materials, for example, of plastic.

In a particularly advantageous further development of the invention, the measuring coil and the compensation coil are arranged relative to each other in one plane, in particular on the same carrier. It is preferred to arrange the compensation coil in concentric relationship with the measuring coil. In this manner, it is possible to arrange the measuring coil and the compensation coil on one carrier or printed circuit board, and to miniaturize them in a particularly advantageous manner. In this connection, it is especially preferred to integrate the eddy current sensor on a printed circuit board together with semiconductors, operational amplifiers, and other components.

In another advantageous further development of the eddy current sensor according to the invention, it is possible to arrange one measuring coil and/or one compensation coil on one side of the test object, whereas another measuring coil and/or another compensation coil are arranged on the opposite side thereof. In the simplest case, the measuring coil is provided as a transmitting coil on one side of the test object, whereas on the opposite side of the test object, the compensation coil is constructed as a receiving coil. Naturally, the receiving coil may also be a further measuring coil for determining the material or geometric parameters of the test object.

It is preferred to design and construct the measuring coil and/or compensation coil as a spiral coil by the planar process. To this end, the measuring coil and/or the compensation coil may be applied by the thin layer or thick layer technique to a carrier material, for example, the material of a printed circuit board. In a further development, it would then also be possible to integrate the evaluation circuit on the carrier material of the measuring coil and/or compensation coil, thus resulting in a particularly advantageous and compact eddy current sensor with temperature compensation.

It would also be possible to make the measuring coil or the compensation coil multilayered. Likewise, it would be possible to separate the measuring coil from the compensation coil by an insulating layer, so that the flat coils are arranged side by side in two layers.

In a particularly preferred further development, the quality of the measuring coil is adapted to the quality of the compensation coil. Preferred is a quality of the measuring coil in an amount equal to the quality of the compensation coil. The quality of the coils may be adapted via the number of winds, the diameter of the coil wire, or the coil geometric.

Preferably, the measurement with the eddy current sensor is noncontacting. The eddy current sensor is used in particular for measuring the thickness of a coating, a conducting path, or a conducting tape. Naturally, however, the eddy current sensor could also lie during the measurement on the surface of the object. However, the surface would have to be constructed as an insulator.

In a further development of the eddy current sensor, the measuring coil and the compensation coil are each interposed in the feedback loop of an operational amplifier of the evaluation circuit. This allows to perform the temperature compensation in a very advantageous manner, when, for example, the outputs of the operational amplifiers are interconnected, and the inputs of the operational amplifiers connect to an oscillator, which generates two complementary, sinusoidal alternating voltages U1 and U2. The complementary, sinusoidal alternating voltages may then be supplied to the noninverting inputs of the amplifier. As a result of the wiring with the complementary alternating voltages, the impedances of the measuring and the compensation coil are automatically subtracted at the junction on the output side between the operational amplifiers, so that the evaluation circuit generates a temperature-compensated output signal.

The evaluation circuit may include means for determining the measuring coil impedance, the compensation coil impedance, and/or the coupling impedance. For example, it is possible to measure and process a voltage signal, which is proportionate to the coupling impedance of the measuring coil. This has the advantage that the coupling impedance of the measuring coil is independent of the distance and the electrical conductivity of the test object in the case of the evaluation circuit according to the invention.

Furthermore, the evaluation circuit may include an electronic device for determining the change of the phase angle of the measuring coil impedance, compensation coil impedance, or coupling impedance. The phase angle may then be used for the further evaluation by the computer of the evaluation circuit.

There exist various possibilities of improving and further developing the teaching of the invention in an advantageous manner. To this end, reference may be made to the following description of respectively several embodiments of the eddy current sensor according to the invention and several variants of the method according to the invention with reference to the drawings.

BRIEF DESCRIPTION OF THE DRAWINGS

The invention is further described in the following schematic drawings, in which.

DETAILED DESCRIPTION OF THE PREFERRED EMBODIMENTS

Figure 1:
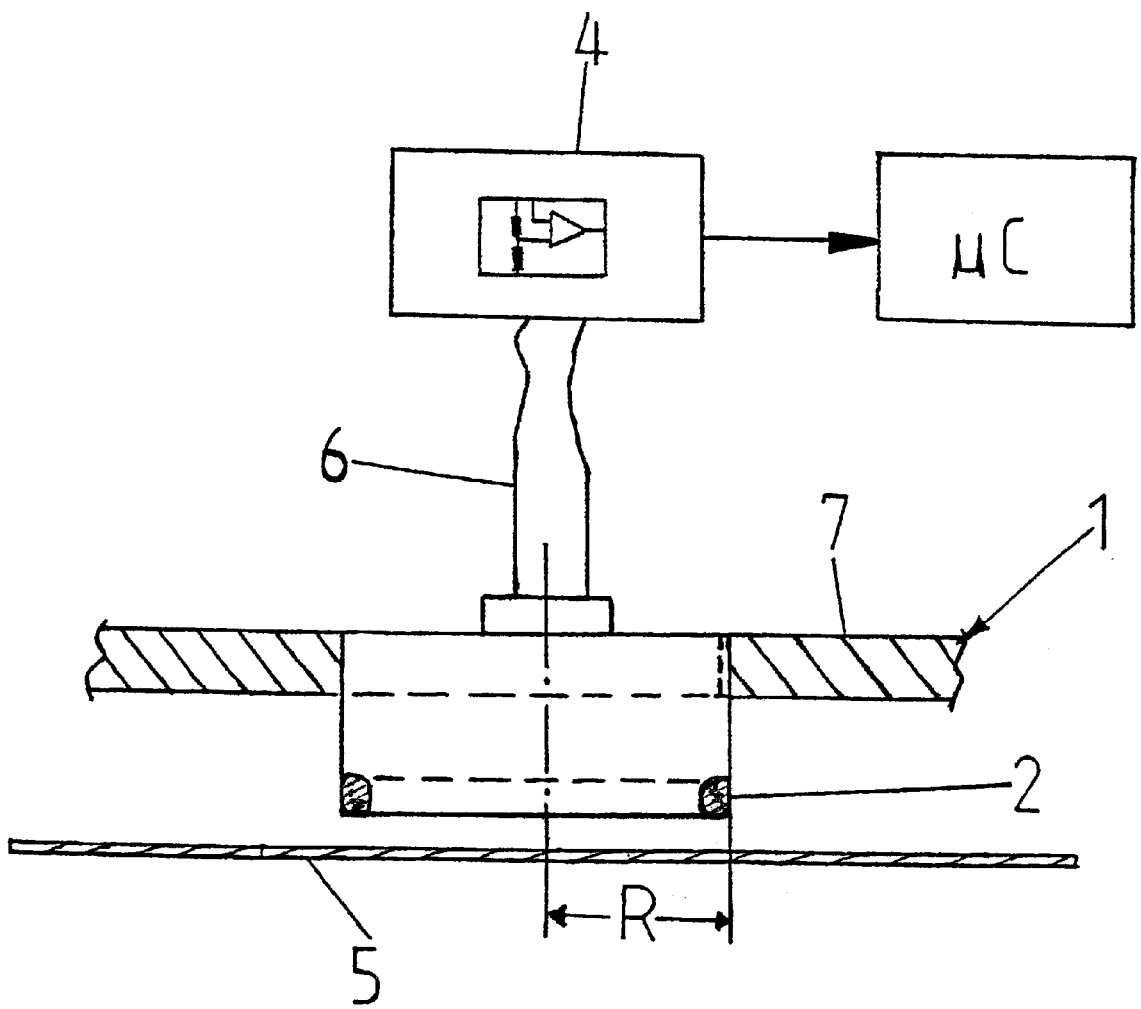
FIG. 1 is a view of a test assembly, which permits determining in accordance with the invention the thickness of a test object by means of a measuring coil unilaterally arranged on the test object.

An eddy current sensor 1 comprises a measuring coil 2, if need be, a compensation coil 3, and an evaluation circuit 4. The evaluation circuit 4 is intended for determining, based on the impedance of measuring coil 2, material and/or geometric parameters, for example, the thickness of an electrically conducting test object 5. For computing the material and/or geometric parameters, the evaluation circuit comprises a microcomputer µC. The measuring coil 2 and compensation coil 3 can be supplied with alternating voltage, and the compensation coil 3 is arranged in the vicinity of measuring coil 2, so that it is exposed to the thermal environmental conditions of measuring coil 2.

For a noncontacting measurement on the flat test object 5, in particular a web, a tape, or a layer, the eddy current sensor 1 is arranged at a distance d from the surface of test object 5. The test object 5 is guided along eddy current sensor 1. To this end, the eddy current sensor may be mounted in the region of a production line for flat materials.

Figure 2A:
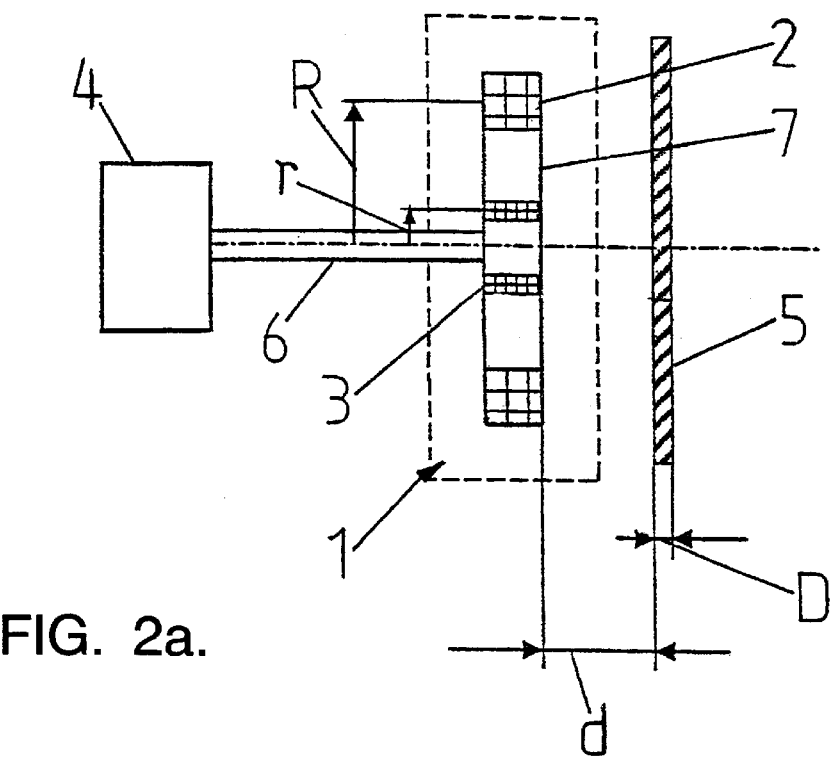
FIG. 2a is a first embodiment of an eddy current sensor of the present invention in the case of the thickness measurement on a flat test object.

As shown in FIG. 2a, the measuring coil 2 of eddy current sensor 1 is designed and constructed as a flat coil, which extends substantially in one plane and comprises only few coil winds extending side by side perpendicularly to the plane. The radius R of the measuring coil is substantially larger than the extension of the coil perpendicularly to the plane. The compensation coil 3 is arranged in concentric or coaxial relationship inside measuring coil 2, and has a smaller radius r. The measuring coil 2 and compensation coil 3 are arranged on a carrier 7, and extend in one plane. Likewise, the compensation coil 3 is designed and constructed as a flat coil.

Both the measuring coil 2 and the compensation coil 3 are supplied with alternating voltage via a line 6. The measuring coil 2 may be supplied with a sinusoidal alternating voltage, and the compensation coil 3 with a sinusoidal alternating voltage complementary thereto. Under similar environmental conditions, the quality of measuring coil 2 should correspond to the quality of compensation coil 3. The adaptation of the coil qualities can be achieved by a corresponding selection of the coil parameters. For example, it is possible to influence the coil quality via the number of winds, the diameter of the coil wire, and the coil geometry. The radius r of the compensation coil is preferably smaller than the spacing d between test object 5 and measuring coil 2.

The eddy current sensor 1 operates as follows: the measuring coil 2 receiving the sinusoidal alternating voltage, in particular its impedance, is influenced by the presence of test object 5. The eddy current effect leads to a change of the complex part of the impedance. As a result of the change in the impedance of measuring coil 2, evaluation circuit 4 determines the thickness D of a flat test object 5.

As a function of the ambient temperature, the impedance of measuring coil 2 is influenced on the one hand, and the conductivity of test object 5 on the other hand. When the conductivity of test object 5 is known, it will be possible to compensate the temperature-dependent impedance change of measuring coil 2 by using the impedance change of compensation coil 3 for compensating the temperature influence. For example, the impedance of compensation coil 3 can be subtracted by evaluation circuit 4 from the impedance of measuring coil 2. To this end, it is necessary that the present test object 5 influence compensation coil 3 as little as possible, so that only the influence of the temperature change becomes effective on the impedance of compensation coil 3. The influence of test object 5 on the impedance may be kept low, for example, in that the radius r of compensation coil 3 is as small as possible. The evaluation circuit 4 will then be able to compute the temperature-compensated value for the thickness D of test object 5 based on the different impedances or impedance changes of measuring coil 2 and compensation coil 3.

When supplying measuring coil 2 and, optionally, compensation coil 3 with an alternating voltage of a first frequency in a first measurement, and with an alternating voltage of a second frequency in a second measurement, it will be possible to compute via evaluation circuit 4, the thickness D from a nonlinear equation system. In this instance, the equation is independent of the conductivity of test object 5 and thus of the temperature influence of the conductivity of test object 5.

Figure 2B:
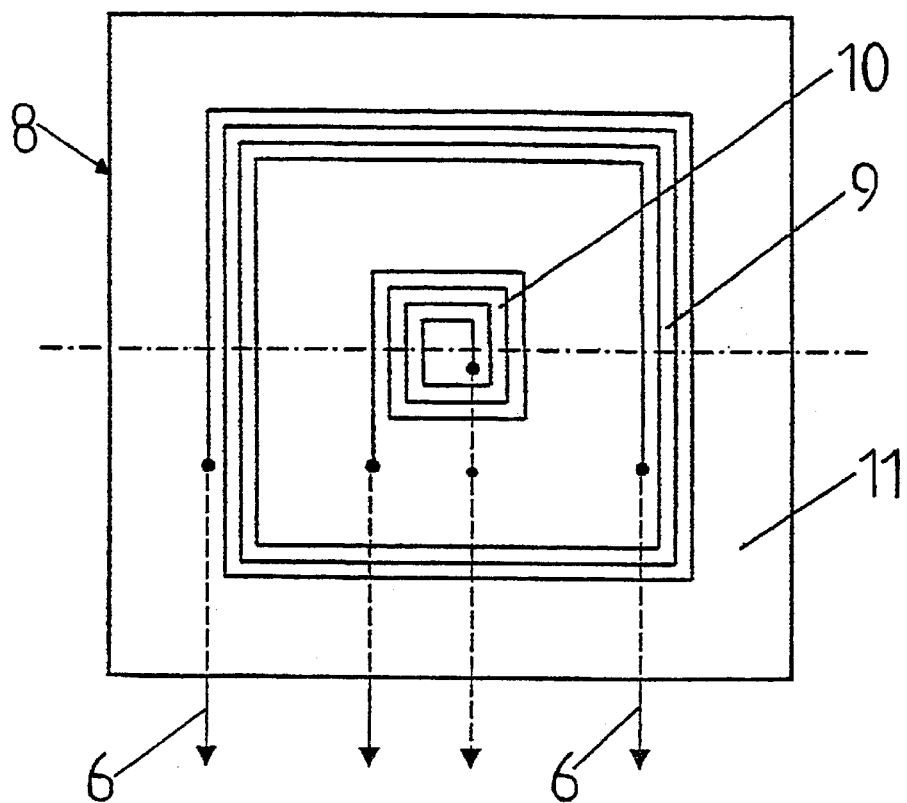
FIG. 2b is a top view of a carrier material with a measuring coil and a compensation coil of the eddy current sensor in accordance with the invention.

FIG. 2b illustrates an eddy current sensor 8 according to a second embodiment, wherein a measuring coil 9 and a compensation coil 10 are applied by the thin layer method to a carrier material 11. The carrier material 11 may be a thin printed circuit board, a plastic, ceramic, or magnetic material, with measuring coil 9 and compensation coil 10 being applied thereto in one layer. The compensation coil 10 is arranged inside measuring coil 9 and in concentric relationship therewith, and both coils 9, 10 are designed and constructed as spiral coils. As an alternative thereto, the coils may also be constructed multilayered, respectively separated by an insulating layer. The dimensions of compensation coil 10 are small in comparison with spacing d between test object 5 and eddy current sensor 8. This allows to reduce the electromagnetic influence of test object 5 on compensation coil 10.

Figure 3:
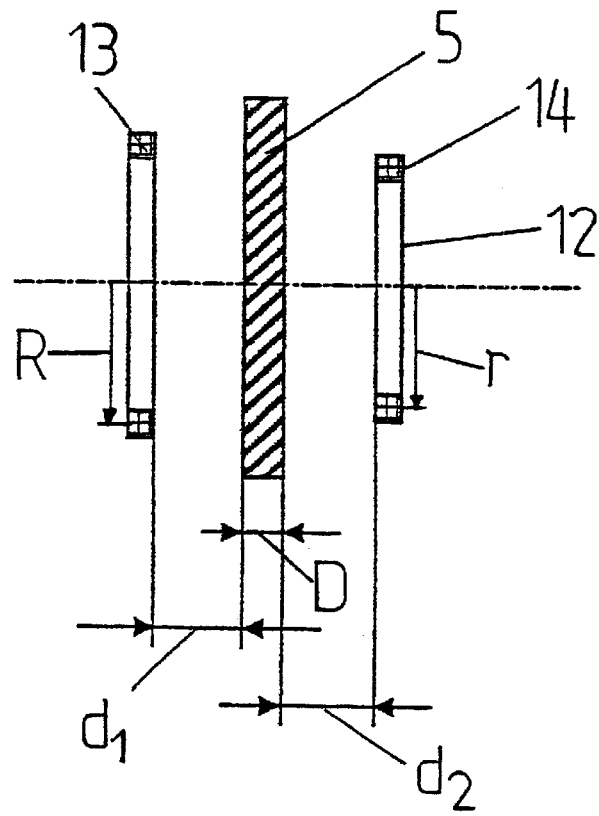
FIG. 3 shows a further eddy current sensor according to the present invention with two opposite coils, one coil serving as a transmitting coil and a further coil as a receiving coil.

In FIG. 3, an eddy current sensor 12 is provided with a measuring coil 13 and a compensation coil 14. The measuring coil 13 is arranged at a distance $d_1$ from test object 5, whereas opposite compensation coil 14 is arranged at a distance $d_2$ from test object 5. In this embodiment, the measuring coil 13 is used as a transmitting coil, and compensation coil 14 serves as a receiving coil. The radius r of compensation coil 14 is smaller than radius R of measuring coil 13.

As an alternative to this embodiment, it would be possible to provide, instead of arranging one measuring coil 13 and one compensation coil 14 on both sides of test object 5, respectively one measuring coil on both sides of test object 5. A temperature compensation of the impedance of measuring coil 13 by a compensation coil would then be omitted, so that only a temperature compensation would be provided via the evaluation circuit as regards the conductivity of test object 5.

Figure 4:
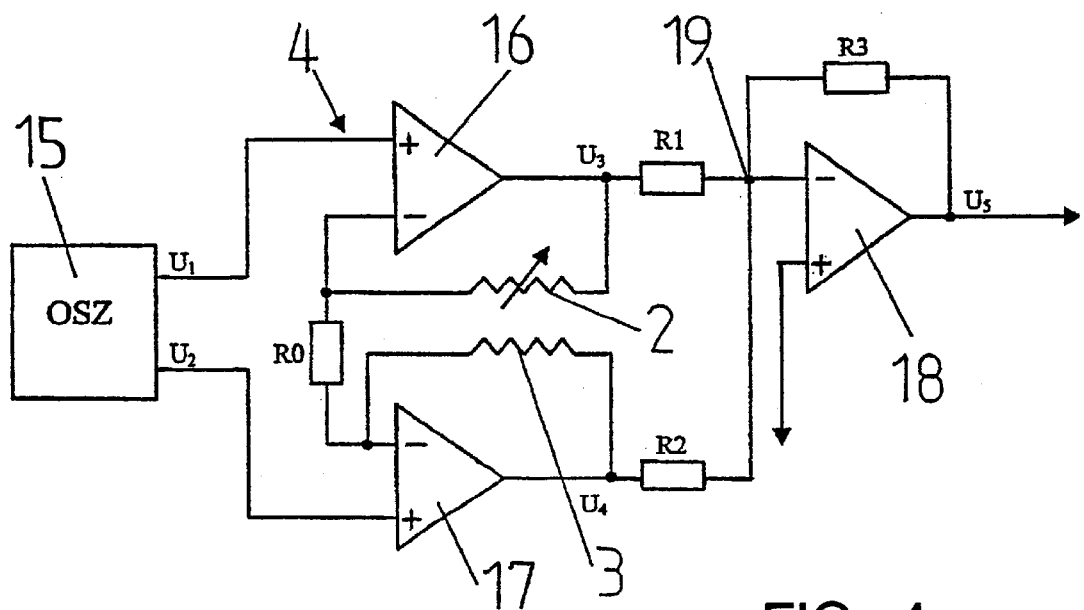
FIG. 4 shows an evaluation circuit of the eddy current sensor for determining a temperature-compensated measured value for material and geometric parameters of electrically conducting materials.

FIG. 4 illustrates the evaluation circuit 4 of eddy current sensors 1, 8, and 12 respectively. The evaluation circuit 4 comprises an oscillator 15 and a plurality of operational amplifiers 16–18. The wiring of the operational amplifiers 16–18 also includes resistors R0, R1, R2, and R3.

The oscillator 15 generates two complementary, sinusoidal alternating voltages $U_1$, and $U_2$, which are supplied to the noninverting inputs of operational amplifiers 16 and 17. The measuring coil 2 and compensation coil 3 are each interposed in the feedback of operational amplifiers 16, 17. The operational amplifiers 16, 17 are used as measuring amplifiers for determining the impedances of measuring coil 2 and compensation coil 3. At junction 19, a potential results, which depends on the impedance of measuring coil 2 and the impedance of compensation coil 3, and forms a temperature-compensated measuring signal. The measuring signal at junction 19 is again amplified by operational amplifier 18, so that an output signal $U_5$ results at the output of operational amplifier 18. This output signal $U_5$ is supplied to a microcontroller of the evaluation circuit, where a further computation proceeds. Preferably, this computation is based on the disclosed method of the present invention. In this process, an additional temperature compensation of the conductivity of the test object occurs by the computation with the nonlinear equation system.

The output signal $U_3$ of operational amplifier 16, which is wired for use as measuring amplifier, corresponds to the equation:

$$U_3 = \frac{U_1 K_1 Z_2 - U_2 K_2 Z_3}{R0}, \quad Z_2 = f(Temp), Z_3 = f(Temp).$$

where K1=R3/R1, K2=R3/R2. $Z_2$ and $Z_3$ are the complex impedances of measuring coil 2 and compensation coil 3. The signal $U_3$ is proportionate to the coupling impedance $dZ_2$ of measuring coil 2, since $Z_3$ is independent of the distance and the electrical conductivity of test object 5. The temperature compensation occurs by simply subtracting the complex impedances $Z_2$ and $Z_3$ of measuring coil 2 and compensation coil 3, without requiring a more extensive computation, since the differential voltage signal automatically adjusts itself at junction 19 as a result of the wiring of evaluation circuit 4 and the supply with two complementary, sinusoidal alternating voltages $U_1$, and $U_2$.

Figure 5:
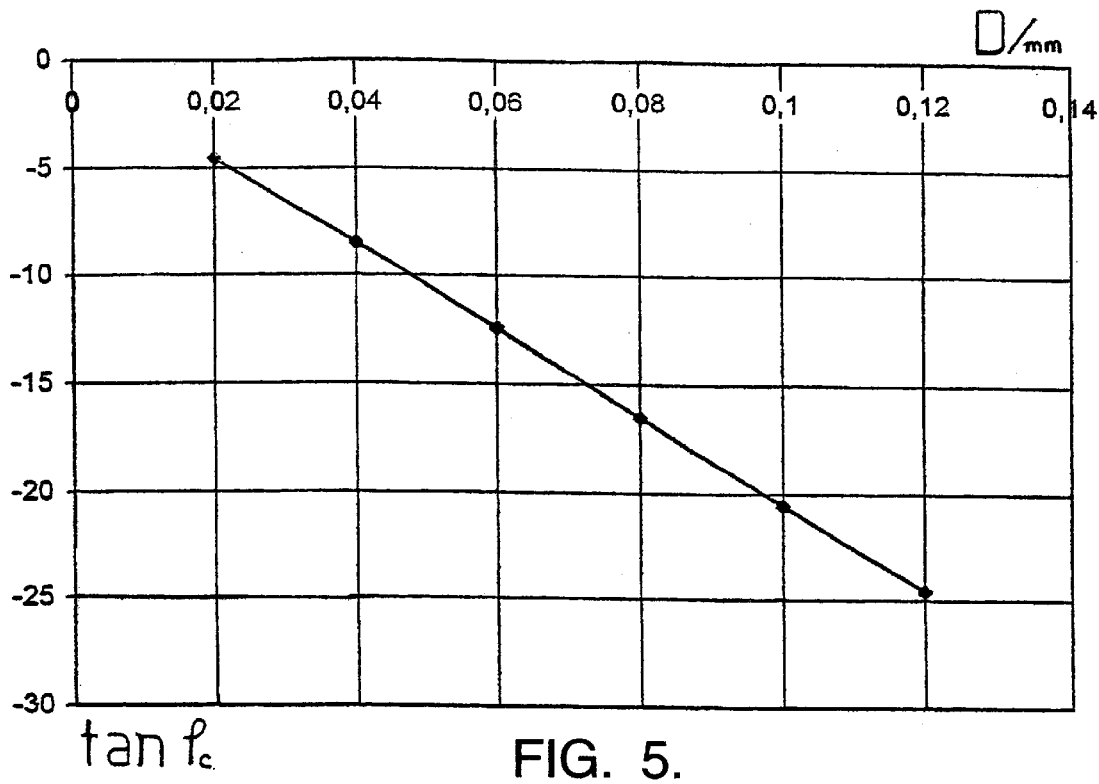
FIG. 5 is a diagram with a function, which illustrates the relationship between tan $\phi_c$ and the thickness D of the test object.

FIG. 5 illustrates a measuring curve, which shows the relation between tan $\phi_c$ and the thickness D of test object 5. The formula for computing tan $\phi_c$ has been presented in connection with the method of the invention, and the diagram shows the values for tan $\phi_c$ as computed by the microcontroller of evaluation circuit 4, so that one can note therefrom the proportional relationship between computed value tan $\phi_c$ and real thickness D of test object 5.

The tan $\phi_c$ as is present at the output of the microcontroller of evaluation circuit 4, results from dividing the temperature-compensated imaginary part by the temperature-compensated real part of the coil impedances. The tan $\phi_c$ can be computed irrespective of the conductivity of the test object, according to the nonlinear differential equation based on two impedance values measured at the first frequency and the second frequency of the alternating voltage supplied to measuring coil 2 and to compensation coil 3.

Figure 6:
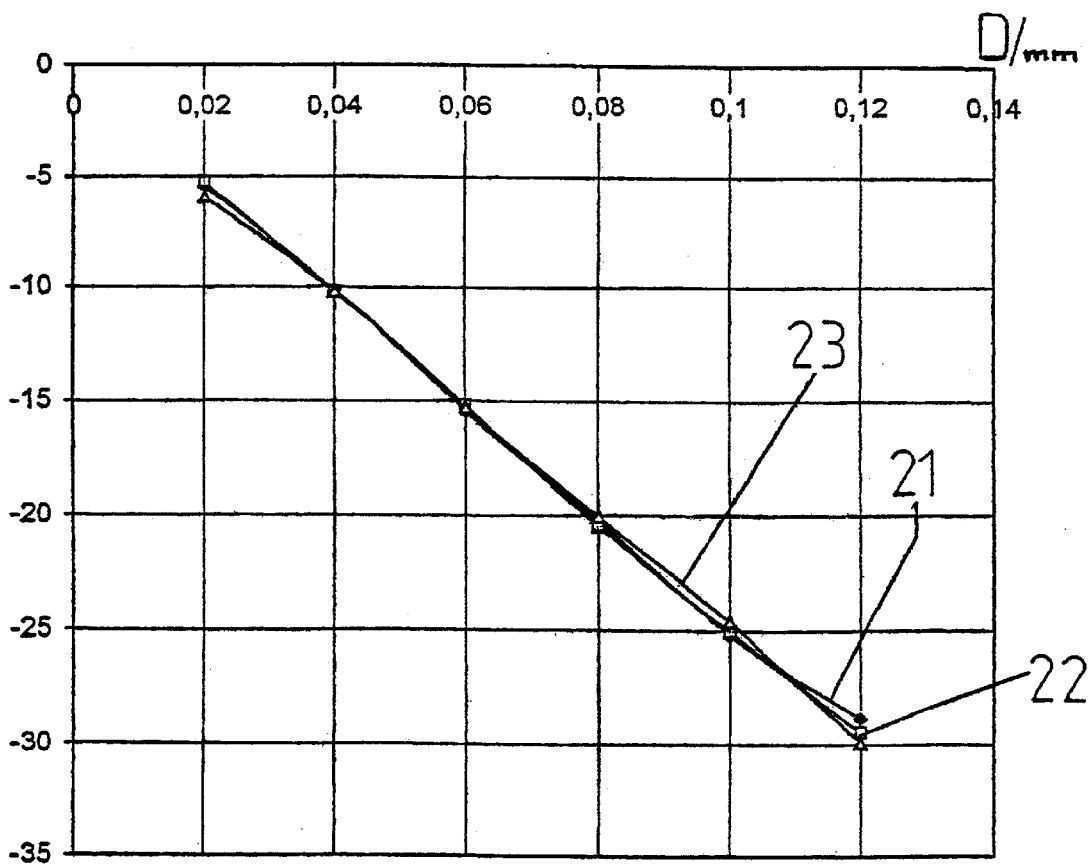
FIG. 6 is a diagram with functions, which illustrate the relationship between tan $\phi_c$ and the thickness D of the test object, wherein the individual curves illustrate the measuring results with a different spacing between the test object and the measuring coil.

FIG. 6 illustrates again the relation between tan $\phi_c$ and the thickness D of test object 5, wherein the spacing between test object 5 and measuring coil 2 is shown as parameter. The functions 21, 22, 23 plotted in FIG. 6 show that the determination of D by the nonlinear differential equation is nearly independent of the distance d of test object 5 from measuring coil 2. As a result, a costly, exact alignment of test object 5 to a certain distance d from measuring coil 2 of eddy current sensor 1 becomes unnecessary.

The method of the present invention leads to excellent measuring results of the eddy current process, since as a result of measuring at two different frequencies of the alternating current that is supplied to measuring coil 2 and compensation coil 3, the output signals of evaluation circuit 4 are independent of the temperature-dependent conductivity of test object 5. The eddy current sensor of the present invention permits compensating in addition the temperature influence on the impedance of measuring coil 2, so that in the end the measuring results are cleared of falsifications by the temperature.

As regards the method of the invention, the formulae needed for the computation by evaluation circuit 4 are shown in the following:

When the conductivity σ of test object 5 is known, the thickness D of test object 5 can be determined by the following equations:

(EQUATION 1)

$$D \approx konst. * \tan\varphi_c = -\frac{\varphi_2(\xi, \beta)}{\varphi_1(\xi, \beta)} \quad \xi = \frac{2d}{r} \quad \beta = r\sqrt{\mu_0 \omega \sigma}$$

$\psi_1(\xi,\beta) = \frac{3}{2}([\frac{3}{2}ch(\xi m) - \cos(\xi n)] + m*sh(\xi m) + n*\sin(\xi n))$ $\psi_2(\xi,\beta) = mn(ch(\xi m) - \cos(\xi n)) + \frac{3}{2}(n*sh(\xi m) - m*\sin(\xi n))$ $$m = \frac{1}{\sqrt{2}}\sqrt{\sqrt{\frac{81}{16} + \beta^4} + \frac{9}{4}}, \quad n = \frac{1}{\sqrt{2}}\sqrt{\sqrt{\frac{81}{16} + \beta^4} - \frac{9}{4}},$$

where d is the spacing between measuring coil 2 and test object 5, r the radius of measuring coil 2 and compensation coil 3 respectively, $\mu_o$ the magnetic field constant, and ω the angular frequency.

Proceeding from the foregoing equations, it is possible to determine for a limited $$\beta = r\sqrt{\omega\mu_o\sigma} \geq 10$$

the value for tan $\phi_c$ by the following simplified equation:

(EQUATION 2)

$$\tan\varphi_c = -2\beta\frac{2\sqrt{2}\beta(ch(\delta) - \cos(\delta)) + 3(sh(\delta) - \sin(\delta))}{3\sqrt{2}(ch(\delta) - 2\cos(\delta)) + 2\beta_k(sh(\delta) + \sin(\delta))},$$

$$\delta = \frac{\xi\beta}{\sqrt{2}}$$

For a further limited β and ξβ<1, tan $\phi_c$ can be approximated by the following equation:

(EQUATION 3)

$$\tan\varphi_c = -\frac{\beta^2\xi(2+\xi)}{3\left(3\xi + 4 + \frac{3}{2}\xi^2\right)}.$$

In the nonlinear equation systems as used in the method of the invention, tan ø is determined at a first and a second frequency, and tan $\phi_c$ results by computation from the nonlinear equation system:

(EQUATION 4)

$$\tan\varphi_c(\omega_k) = -\frac{\varphi_2(\xi, \beta_k)}{\varphi_1(\xi, \beta_k)}, \quad \beta_k = r\sqrt{\mu_0\omega\sigma}, k = 1, 2$$

For a limited β, it is possible to determine tan $\phi_c$ as:

$$D \approx konst. * \tan\varphi_c = \qquad \text{(Equation 5)}$$

$$-2\beta_k\frac{2\sqrt{2}\beta_k(ch(\delta_k) - \cos(\delta_k)) + 3(sh(\delta_k) - \sin(\delta_k))}{3\sqrt{2}(3ch(\delta_k) - 2\cos(\delta_k)) + 2\beta_k(sh(\delta_k) + \sin(\delta_k))},$$

-continued $$\delta_k = \frac{\xi \beta_k}{\sqrt{2}}$$

The angular frequency $\omega_1$ is selected so large that the impedance of the measuring coil becomes independent of the thickness of the foil. With that, it is possible to compute the conductivity.

$$\sigma = -\frac{9\tan\varphi(\omega_1)}{2\mu_o\omega_1 r^2} \quad \text{(Equation 6)}$$

A known conductivity is assumed, wherein $\omega$ is equated with $\omega_2$. The amplitude of the coupling impedance may additionally be used for a numerical correction and improvement of the computation.

When $\sigma$ and $\mu_2$, as well as tan ø are known, the measurement can be conducted at a frequency $\omega_1$, so that the thickness D can be measured via Equation 1. In this instance:

$$\beta = 2\sqrt{\omega_1 \mu_o \sigma}.$$

When $\sigma$ or $\mu_o$ are unknown, it will be necessary, as described, to measure at two frequencies $\omega_1$ and $\omega_2$, so that it is possible to determine the thickness D.

What is claimed is:

1. A method for operating an eddy current sensor having a measuring coil, a compensation coil, and an evaluation circuit for determining material or geometric parameters of a test object, comprising the steps of
    positioning the test object at a predetermined distance from the measuring coil and the compensating coil,
    measuring the impedance of the measuring coil while the measuring coil is being supplied with an alternating voltage of a first predetermined frequency, then
    measuring the impedance of the measuring coil while the measuring coil is being supplied with an alternating voltage of a second predetermined frequency which is different from said predetermined frequency, and
    computing in the evaluation circuit the material and geometric parameters of the test object based on the impedances of the measuring coil at the first and second frequencies, and including compensating for temperature influences on the measured impedances of the measuring coil with a measured impedance of the compensation coil.

2. The method as defined in claim 1 wherein the compensation coil is positioned so that the test object has substantially no influence on its impedance.

3. The method as defined in claim 2 wherein the compensation coil is spatially smaller than the measuring coil and is arranged inside the measuring coil.

4. The method as defined in claim 2 comprising the further steps of computing the conductivity of the test object in the evaluation circuit based upon the measured value of the impedance at at least one of the predetermined frequencies, and computing the thickness of the test object based upon the computed conductivity.

5. The method as defined in claim 1 wherein the first frequency is sufficiently high so that its impedance is substantially independent of the material and geometric parameters of the test object.

6. The method as defined in claim 1 wherein the computing step includes utilizing a nonlinear system which is dependent on the first frequency and the second frequency of the alternating voltage.

7. The method as defined in claim 1 wherein the computing step includes computing the thickness (D) of the test object from the following equation:

$$D \approx konst. * \tan\varphi_c = -2\beta_k \frac{2\sqrt{2}\,\beta_k(ch(\delta_k) - \cos(\delta_k)) + 3(sh(\delta_k) - \sin(\delta_k))}{3\sqrt{2}\,(3ch(\delta_k) - 2\cos(\delta_k)) + 2\beta_k(sh(\delta_k) + \sin(\delta_k))}.$$

8. The method as defined in claim 1 wherein the computing step is limited to a range as a function of the conductivity of the test object and the first and second frequencies.

9. The method as defined in claim 1 wherein the range, to which the computation of the evaluation circuit is limited, is predetermined by the following equation:

$$r\sqrt{\omega_k \mu_o \sigma_k} \geq 10.$$

10. The method as defined in claim 1 wherein the temperature compensating step includes subtracting the complex impedance of the measuring coil from the complex impedance of the compensation coil.

11. A method for operating an eddy current sensor having a measuring coil, and an evaluation circuit for determining material or geometric parameters of a test object, comprising the steps of
    positioning the test object at a first predetermined distance from the measuring coil which is greater than twice the radius of the measuring coil and measuring the impedance or the inductance value and/or the damping value of the measuring coil when supplied with an alternating voltage at a given frequency,
    positioning the test object at a second predetermined distance from the measuring coil which is less than twice the radius of the measuring coil and measuring the impedance or the inductance value and/or the damping value of the measuring coil when supplied with an alternating current at the given frequency, and
    computing in the evaluation circuit the material and geometric parameters of the test object based on the values measured at the first and second distances.

12. The method as defined in claim 11 comprising the further steps of determining the conductivity of the test object, and computing in the evaluation circuit the thickness of the test object based upon the measured values at the first and second distances and the conductivity.

13. An eddy current sensor comprising
    a measuring coil and a compensation coil which are each adapted for receiving an alternating current, and with the compensation coil arranged in the vicinity of the measuring coil so that it is exposed to the thermal environmental conditions of the measuring coil,
    an evaluation circuit connected to the measuring coil and the compensation coil for determining material and/or geometric parameters of an electrically conductive test object from the impedances of the measuring coil and the compensation coil, and
    the compensation coil being designed and arranged such that the test object has substantially no influence on its impedance.

14. The eddy current sensor as defined in claim 13 wherein the compensation coil is spatially smaller than the measuring coil.

15. The eddy current sensor as defined in claim 13 wherein the radius of the compensation coil is smaller than the radius of the measuring coil, and smaller than the spacing between the compensation coil and the test object.

16. The eddy current sensor as defined in claim 13 wherein the compensation coil is a flat coil and arranged in one plane, and wherein the compensation coil is arranged inside the measuring coil.

17. The eddy current sensor as defined in claim 13 wherein the measuring coil and the compensation coil are arranged relative to each other in a common plane.

18. The eddy current sensor as defined in claim 13 wherein the measuring coil and the compensation coil are arranged in concentric relationship with each other.

19. The eddy current sensor as defined in claim 13 wherein the measuring coil is arranged on one side of the test object, and the compensation coil is arranged on the opposite side thereof.

20. The eddy current sensor as defined in claim 13 wherein the measuring coil and the compensation coil are designed and constructed as helical coils which lie in a common plane.

21. The eddy current sensor as defined in claim 13 wherein the measuring coil and/or the compensation coil are constructed in multiple layers which are separated by an insulating layer.

22. The eddy current sensor as defined in claim 13 wherein the coil geometry of the measuring coil and that of the compensation coil are substantially the same.

23. The eddy current sensor as defined in claim 13 wherein the measuring coil and the compensation coil are each interposed in the feedback loop of an operational amplifier which is part of the evaluation circuit.

24. The eddy current sensor as defined in claim 13 wherein the evaluation circuit includes means for generating two complementary alternating voltages.

25. The eddy current sensor as defined in claim 24 wherein the two complementary alternating voltages are each applied to an input of an operational amplifier.

26. The eddy current sensor as defined in claim 13 wherein the evaluation circuit includes means for measuring the impedance of the measuring coil, the impedance of the compensation coil, and/or the coupling impedance.

27. The eddy current sensor as defined in claim 13 wherein the evaluation circuit includes an electronic device for determining the change of the phase angle of the measuring coil impedance, compensation coil impedance, and/or coupling impedance.

28. The eddy current sensor as defined in claim 13, wherein the measuring coil and the compensation coil are arranged with substantially parallel axes relative to each other.

29. The eddy current sensor as defined in claim 13, wherein the measuring coil and compensation coil have axes which form an acute angle with each other, or are arranged in orthogonal relationship with each other.

30. The eddy current sensor as defined in claim 13 wherein the compensation coil has a smaller number of winds, or a smaller diameter of the coil wire, or a different material of the wire or coil core, so that the influence of the test object is less than in the case of the measuring coil.

31. The method as defined in claim 11, wherein the eddy current sensor further includes a compensation coil and wherein the computing step includes compensating for temperature influences on the impedance of the measuring coil utilizing the measured impedance of the compensation coil.

32. The method as defined in claim 31 wherein the compensation coil is spatially smaller than the measuring coil.

* * * * *